(12) United States Patent
Ostrovsky et al.

(10) Patent No.: US 9,113,990 B2
(45) Date of Patent: Aug. 25, 2015

(54) IMPLANTS AND METHODS FOR ENHANCING IN-VIVO ULTRASOUND IMAGES OF THE SAME

(75) Inventors: Isaac Ostrovsky, Wellesley, MA (US); Jianmin Li, Lexington, MA (US); Tim Harrah, Cambridge, MA (US); Jozef Slanda, Milford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 558 days.

(21) Appl. No.: 13/177,241

(22) Filed: Jul. 6, 2011

(65) Prior Publication Data

US 2012/0029273 A1 Feb. 2, 2012

Related U.S. Application Data

(60) Provisional application No. 61/368,785, filed on Jul. 29, 2010.

(51) Int. Cl.
| | |
|---|---|
| *A61F 2/04* | (2013.01) |
| *B32B 37/14* | (2006.01) |
| *A61F 2/00* | (2006.01) |
| *A61B 5/00* | (2006.01) |
| *A61B 8/08* | (2006.01) |

(52) U.S. Cl.
CPC ............ *A61F 2/0045* (2013.01); *A61B 5/686* (2013.01); *A61B 8/0833* (2013.01); *A61B 8/481* (2013.01); *A61F 2250/0098* (2013.01); *Y10T 156/10* (2015.01); *Y10T 156/1062* (2015.01)

(58) Field of Classification Search
CPC ...... A61B 5/686; A61B 8/0833; A61B 8/481; A61F 2250/0098; A61F 2/0045
USPC .................. 600/29–32, 37; 128/897–899
See application file for complete search history.

(56) References Cited

U.S. PATENT DOCUMENTS

| | | | | |
|---|---|---|---|---|
| 6,106,473 | A * | 8/2000 | Violante et al. | 600/458 |
| 6,306,094 | B1 * | 10/2001 | Joseph | 600/458 |
| 2004/0093069 | A1 * | 5/2004 | Priewe et al. | 623/1.15 |
| 2009/0281635 | A1 * | 11/2009 | Li et al. | 623/23.66 |

OTHER PUBLICATIONS

Search Report and Written Opinion for International Application No. PCT/US2011/043210, mailed Aug. 25, 2011, 11 pages.

\* cited by examiner

*Primary Examiner* — Christine H Matthews
*Assistant Examiner* — Joshua D Lannu
(74) *Attorney, Agent, or Firm* — Brake Hughes Bellermann LLP

(57) ABSTRACT

An implant includes a substrate and a carrier coupled to the substrate. The carrier including a plurality of objects configured to reflect energy emitted by an ultrasound device. In some embodiments, the carrier includes a plurality of air bubbles that are configured to reflect energy emitted by an ultrasound device. In one embodiment, a method of forming a bodily implant includes forming a substrate, disposing a plurality of air bubbles within a carrier, and applying the carrier to the substrate.

18 Claims, 3 Drawing Sheets

IMPLANTS AND METHODS FOR ENHANCING IN-VIVO ULTRASOUND IMAGES OF THE SAME

CROSS-REFERENCE TO RELATED APPLICATION

This application is a Nonprovisional of, and claims priority to, U.S. Patent Application Ser. No. 61/368,785, filed Jul. 29, 2010, entitled "IMPLANTS AND METHODS FOR ENHANCING IN-VIVO ULTRASOUND IMAGES OF THE SAME", which is incorporated by reference herein in its entirety.

TECHNICAL FIELD

This disclosure relates generally to bodily implants and more particularly to bodily implants that include features for enhancing in-vivo ultrasound images.

BACKGROUND

A variety of medical procedures include placing implants within a body of a patient. Some medical procedures include placing implants within a body of a patient such that the implant provides support to a portion of the body of the patient. For example, some medical procedures are performed to treat various female pelvic dysfunctions, including procedures to treat urinary incontinence, and correcting various prolapse conditions such as uterine prolapse, cystoceles, rectoceles, and vaginal vault prolapse.

Some of the implants that are placed within a body of a patient are formed of a plastic material. For example, some implants are formed of a plastic mesh material.

Often times it is desirable to view an implant that has been disposed within a body of a patient. For example, it may be desirable to view an implant during an implantation procedure to confirm that the implant is located in the correct location within the body. Additionally, it may be desirable to view an implant after an implantation procedure to confirm that the implant has not moved from its implanted position.

Implants disposed within a body of a patient can be viewed using imaging devices such as x-ray devices and ultrasound devices. Such imaging devices, however, may not provide adequate views of plastic implants.

Accordingly, it would be desirable to provide an implant that could be viewed with an imaging device during or after an implantation procedure. It would also be desirable to provide a plastic implant that could be viewed with an imaging device during or after an implantation procedure.

SUMMARY

An implant includes a substrate and a carrier coupled to the substrate. The carrier including a plurality of objects configured to reflect energy emitted by an ultrasound device. In some embodiments, the carrier includes a plurality of air bubbles that are configured to reflect energy emitted by an ultrasound device. In one embodiment, a method of forming a bodily implant includes forming a substrate, disposing a plurality of air bubbles within a carrier, and applying the carrier to the substrate.

DETAILED DESCRIPTION

The devices and methods described herein are generally directed to implants and medical devices that are configured to be placed within a body of a patient. In some embodiments, the implants are placed with a body of a patient and positioned to provide support to a portion of the body of the patient. For example, in some embodiments, the implants include, but are not limited to, implants that are placed within a pelvic region of a patient. Such implants can be placed into the pelvic space of a patient and secured at any of several locations within the pelvic space to treat many different pelvic floor dysfunctions. For example, an implant can be secured to a sacrospinous ligament or a ureterosacral ligament for uterine preservation (e.g., if a prolapsed uterus is otherwise healthy, a hysterectomy is not preformed and the uterus is re-suspended with an implant), or for posterior support. In another embodiment, an implant can be secured to pubo-urethral tissue or an obturator muscle (e.g., internus or externus) or membrane (each also referred to herein as "obturator") to treat, for example, incontinence. In yet another embodiment, an implant can be secured to a sacrospinous ligament or an arcus tendineus fascia pelvis (i.e., white line) (also referred to herein as "arcus tendineus") for paravaginal repairs including, for example, cystoceles, rectoceles and enteroceles. An implant can also be secured to various combinations of such locations. The implants described herein may be used in a female patient or a male patient.

Figure 1:
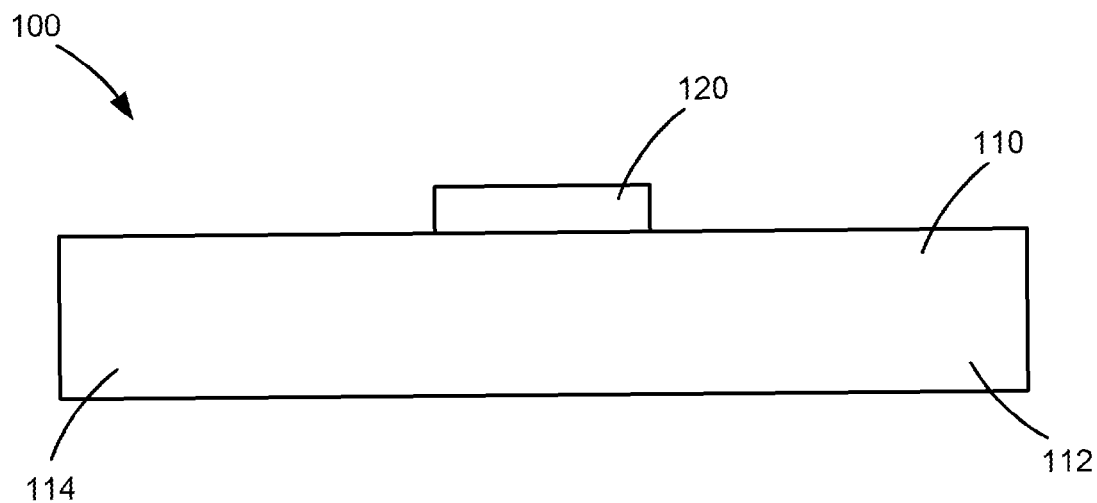
FIG. 1 is a schematic illustration of an implant according to an embodiment.

FIG. 1 is a schematic illustration of an implant 100 according to an embodiment of the invention. The implant includes a substrate 110 and a carrier 120 coupled to the substrate 110. The implant 100 and the substrate 110 can be of any size or shape. In some embodiments, the implant is configured to be placed with a body of a patient. For example, in some embodiments, the implant 100 is configured to be placed within a body of a patient and configured to provide support to a portion of the body of the patient. In other embodiments, the implant 100 is configured to be placed within a body of a patient for a purpose other than providing support to a portion of the body.

In the illustrated embodiment, the substrate 110 includes end portions 112 and 114 and is configured to be placed within a body of a patient to provide support to a portion of the body of the patient. For example, in some embodiments, the substrate 110 of the implant 100 is configured to be placed proximate or adjacent a bladder of a patient to provide support to a portion of the bladder of the patient. In other embodiments, the substrate 110 of the implant 100 is configured to support the urethera or bladder neck of a patient. In yet other embodiments, the substrate 110 of the implant 100 is configured to be placed adjacent another portion of the body to provide support to another portion of the body.

The first end portion 112 and the second end portion 114 are configured to be disposed within bodily tissue of the patient. In some embodiments, the first end portion 112 and the second end portion 114 are configured to be coupled to such bodily tissue to help secure the substrate 110 in place within the body of the patient.

The first end portion 112 and the second end portion 114 can be of any shape or size suitable for extending between a medial portion of the substrate 110 and the bodily tissue. Additionally, the implant 100 may include additional arm members or end portions that are configured to couple to bodily tissue to help secure the implant 100 in place within the body of the patient.

In some embodiments, the first end portion 112 and the second end portion 114 are configured to be disposed within and coupled to an obturatator membrane of the patient or other pelvic tissue of the patient. In other embodiments, the first end portion 112 and the second end portion 114 are configured to be coupled to other bodily tissue.

In some embodiments, the first end portion 112 and the second end portion 114 include tangs or tanged portions configured to help anchor the end portions 112 and 114 within the bodily tissue of the patient. The terms "tanged" or "tangs" as used herein mean roughened or jagged edges or areas, such as can result from cutting a woven or knit mesh material. In other embodiments, the end portions 112 and 114 include barbs, dimples and/or other protrusions configured to engage the bodily tissue of the patient to help retain the implant 100 in place within the body of the patient. In other embodiments, other mechanisms may be used to couple the end portions 112 and 114 to the bodily tissue.

The substrate 110 can be formed of any material. For example, in some embodiments, the substrate 110 is formed of a biologically compatible material. In some embodiments, the substrate 110 is formed of a mesh material, such as a polypropylene mesh, to allow tissue in-growth to the substrate 110 after implantation within the body of the patient. For example, some or all of the substrate 110 can be formed with a mesh material as described in U.S. Patent Pub. 2005/0038452 A1 to Chu, the entirety of which is hereby incorporated by reference. In some embodiments, some or all of an substrate 110 can be formed with the Advantage™ Mesh or the Polyform™ Synthetic Mesh material each provided by Boston Scientific Corporation.

The substrate 110 can be monolithically formed or alternatively, the substrate 110 can be formed with multiple different materials and/or can include multiple different components or portions coupled together. In some embodiments, the substrate 110 can be formed with a combination of materials including synthetic and biological materials. For example, the substrate 110 can be formed with a first biocompatible material and the end portions 112 and 114 can be formed with a second biocompatible material different than the first material. In other embodiments, the substrate 110 is formed with a biological material, and the end portions 112 and 114 are formed with a synthetic material. In some embodiments, the end portions 112 and 114 and the support member 110 have a different weave, pitch, texture, color, and pattern from each other.

In some embodiments, the end portions 112 and 114 and the substrate 110 can be coupled in an abutting relationship, an overlapping relationship, or can be bridged. The end portions 112 and 114 can be coupled to the substrate 110 by, for example, heat bonding, gluing, using fasteners, and/or sewing. In some embodiments, an end portion or arm member can include a heat seal along its length or a portion of its length to help prevent or reduce stretching of the end portion or arm member.

The carrier 120 is coupled to the substrate 110. Any known mechanism may be used to couple the carrier 120 to the substrate 110. For example, in some embodiments, an adhesive or other type of material may be used to couple the carrier 120 to the substrate 110. In some embodiments, the carrier 120 itself is configured to adhere to the substrate 110.

The carrier 120 can be formed of any material, such as a biocompatible material. In some embodiments, the carrier 120 is formed of an adhesive. In some embodiments, the carrier 120 is formed of a plastic material. For example, in some embodiments, the carrier 120 is formed of a polyurethane material.

In some embodiments, the carrier 120, or a portion of the carrier 120, is detectable by an imaging device such as an x-ray or ultrasound device. In some embodiments, the carrier 120 includes an object that is configured to be detectable by an imaging device such as an x-ray or ultrasound device.

In some embodiments, the carrier 120 includes an object that is configured to reflect energy emitted by an ultrasound device. For example, in some embodiments, the carrier 120 includes air or air bubbles 122 disposed or trapped within the carrier 120. The air or the air bubbles 122 are configured to reflect the energy emitted by an ultrasound device such that the air or air bubbles 122 are detectable by the ultrasound device.

For example, in some embodiments, an ultrasound device detects objects by generating and radiating a mechanical waves of a high frequency (i.e., 2-40 MHz). The radiated waves propagate through tissue and reflect at the interface of different materials. Specifically, the more dissimilar the materials at the interface are, the more the waves are reflected. The reflected waves are reflected back to and detected by the transducer of the ultrasound device. The transducer receives the reflection and generates an image. The more reflected waves there are, the better the image is.

Because the difference in mechanical properties of tissue and air is very high, air is a good reflector of ultrasound waves. Specifically, in some embodiments, the portion of ultrasound energy that is reflected from an interface can be determined by the formula:

$$P=\{(Z1-Z2)/(Z1+Z2)\}^2$$

Where Z1 and Z2 are the impedances of the media through which the energy is propagating and the material from which the object is made of. For example, in one embodiment, where an ultrasound device is used in muscle tissue with a polypropylene object disposed therein, the impedance of the muscle tissue is about 1.5 MRayls (MRayls=(Kg/S×M$^2$)106) and the impedance of the polypropylene object is about 2.4 MRayls. Thus, the portion of reflected energy is:

$$P=\{(1.5-2.4)/(1.5+2.4)\}^2=0.053 \text{ or } 5.3\%$$

In some embodiments, the impedance of air is about 0. Thus, the portion of ultrasound energy reflected by an air bubble trapped in muscle tissue is about:

$$P=\{(1.5-0)/(1.5+0)\}^2=1 \text{ or } 100\%$$

Thus, in some embodiments, the almost all of the ultrasound energy is reflected from the tissue-air interface.

In some embodiments, the carrier 120 includes objects other than air bubbles that are configured to reflect energy. Specifically, in some embodiments, the carrier 120 includes other objects that are configured to reflect energy emitted from an ultrasound device. For example, in some embodiments, tungsten, which has an acoustic impedance of about 54 MRayls, is included in the carrier 120. Accordingly, for tungsten the reflected energy would be about: P=(1.5−54)/(1.5+54)2=89%. In another embodiment, the carrier 120 includes stainless steel. For stainless steel the acoustic impedance is about 25 and the reflected energy is about 79%.

In some embodiments, the carrier 120 includes a radio-opaque material such as high density metal particles. Accordingly, the carrier 120 is radio-opaque and would be visible or detectable with an x-ray imaging device. For example, particles or micro-particles of elements such as Platinum, which has a density of about 21.4 g/cm$^3$, Gold, which has a density of about 19.3 g/cm$^3$, or Bismuth, which has a density of about 9.8 g/cm$^3$, may be suspended in the carrier 120. Additionally, in some embodiments, the carrier 120 includes salts of heavy metals, such as bismuth subcarbonate or barium sulfate.

In some embodiments, the carrier 120 includes objects that may be detected using an ultrasound device and objects that may be detected by an x-ray imaging device. In such embodiments, the carrier 120 would be visible or detectable with both an ultrasound device and an x-ray imaging device.

Figure 2:
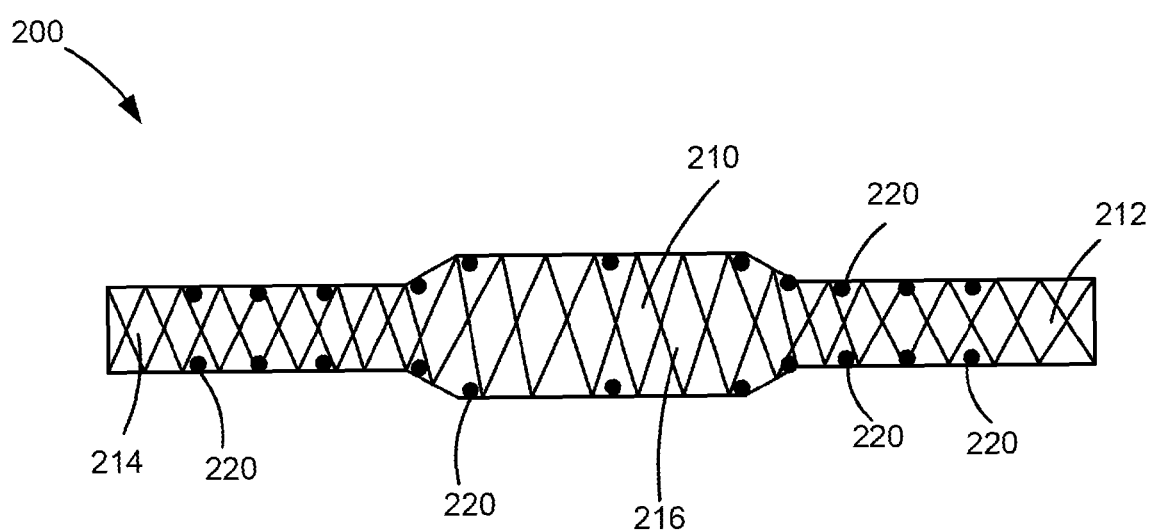
FIG. 2 is a top view of an implant according to an embodiment.
Figure 3:
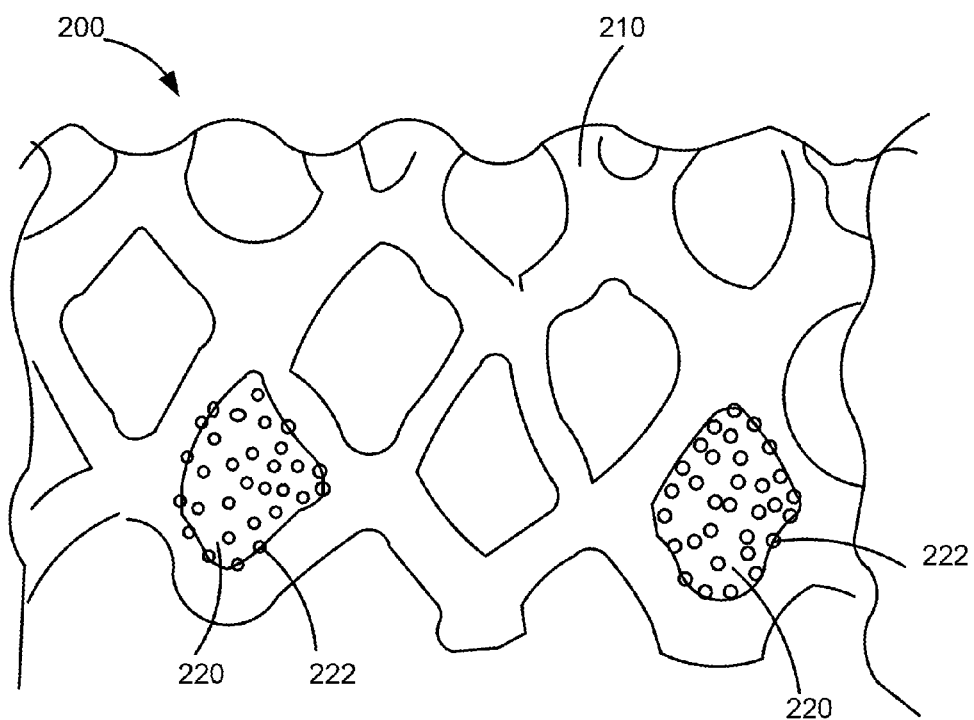
FIG. 3 is a portion of the implant of FIG. 2.

FIGS. 2 and 3 illustrate an implant 200 in accordance with an embodiment. Specifically, FIG. 2 is a top view of the implant 200 and FIG. 3 is a top view of a portion of an edge of the implant 200. The implant 200 includes a substrate 210 and a carrier 220 (not all portions of the carrier 220 are labeled) coupled to the substrate 210. The implant 200 implant is configured to be placed with a body of a patient.

In the illustrated embodiment, the substrate 210 includes end portions 212 and 214 and is configured to be placed within a body of a patient to provide support to a portion of the body of the patient. For example, in some embodiments, the substrate 210 of the implant 200 is configured to be placed proximate or adjacent a bladder of a patient to provide support to a portion of the bladder of the patient. In other embodiments, the substrate 210 of the implant 200 is configured to support the urethera or bladder neck of a patient. In yet other embodiments, the substrate 210 of the implant 200 is configured to be placed adjacent another portion of the body to provide support to another portion of the body.

The first end portion 212 and the second end portion 214 are configured to be disposed within bodily tissue of the patient. In some embodiments, the first end portion 212 and the second end portion 214 are configured to be coupled to such bodily tissue to help secure the substrate 210 in place within the body of the patient.

A medial portion 216 of the substrate 210 has a width that is larger than the width of the end portions 212 and 214. In other embodiments, the substrate includes more than two end portions or arms that are configured to be coupled to bodily tissue. For example, in some embodiments, the implant 200 includes four or six end portions or arms that are configured to be coupled to bodily tissue.

In some embodiments, the first end portion 212 and the second end portion 214 include tangs or tanged portions configured to help anchor the end portions 212 and 214 within the bodily tissue of the patient. In other embodiments, the end portions 212 and 214 include other anchoring features, such as anchors or barbs, that are configured to help retain the implant in place within the body of the patient.

In the illustrated embodiment, the substrate 210 is formed of a polypropylene mesh. In other embodiments, the substrate 210 is formed of another biocompatible material. For example, in some embodiments, some or all of the substrate 210 can be formed with a mesh material as described in U.S. Patent Pub. 2005/0038452 A1 to Chu, the entirety of which is hereby incorporated by reference. In some embodiments, some or all of an substrate 210 can be formed with the Advantage™ Mesh or the Polyform™ Synthetic Mesh material each provided by Boston Scientific Corporation.

The carrier 220 is coupled to the substrate 210. In the illustrated embodiment, the carrier 220 is configured to be applied to the substrate 210 while the carrier 220 is in a liquid form. Once the carrier 220 cools and is dried, it is coupled to the substrate 210. The carrier 120 can be formed of any material, such as a biocompatible material. In the illustrated embodiment, is formed of a polyurethane material. In some embodiments, the carrier 220 is formed of a flexible material.

As best illustrated in FIG. 3, the carrier 220 is disposed within the spaces or interstices defined by the mesh material of the substrate 210. In some embodiments, the carrier 220 is disposed about the entire substrate 210. In other embodiments, as illustrated in FIG. 3, the carrier 220 is disposed or coupled to the substrate 210 in a pattern. In some embodiments, the carrier is disposed within the openings defined by the mesh material. In other embodiments, the carrier is disposed on the mesh material itself. For example, in some embodiments, the carrier is disposed the knots or the intersections of the mesh material.

In some embodiments, the carrier is disposed on the substrate in a pattern. For example, in some embodiments, the carrier is disposed on a perimeter of the substrate. In other embodiments, the carrier is disposed at several locations with a distance between the various locations. In some embodiments, the carrier is disposed on the perimeter of the substrate and at a location or locations toward the middle of the substrate. In such embodiments, the some portion of the carrier would remain on the substrate and would be detectable even if a physician were to cut off the perimeter of the substrate (for example to be placed within a patient of a smaller size).

Figure 4:
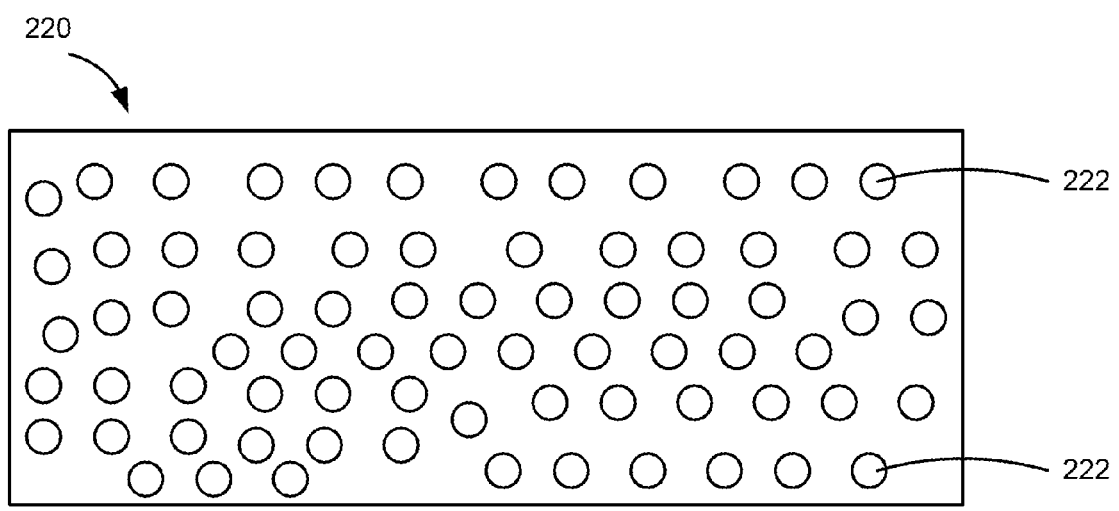
FIG. 4 illustrates a carrier according to an embodiment.

As illustrated in FIG. 4, in the illustrated embodiment, the carrier 220 includes or defines air or air bubbles 222 (only some of the air bubbles 222 are labeled). The air or air bubble are configured to reflect energy emitted by an ultrasound device. Accordingly, the ultrasound device may create an image of the implant 200 while the implant is disposed within bodily tissue.

Figure 5:
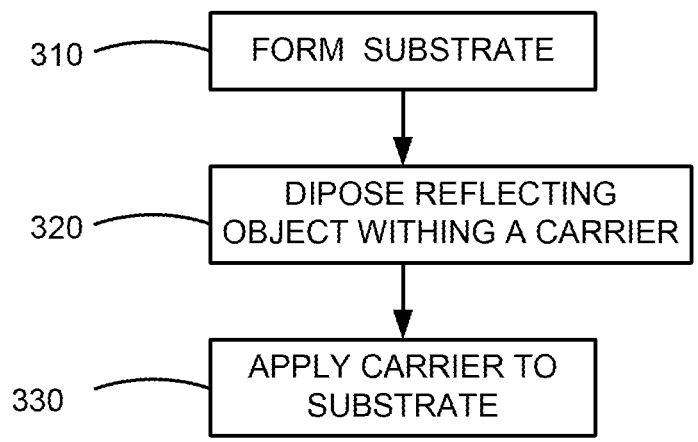
FIG. 5 is a flow chart of a method for forming an implant according to an embodiment.

FIG. 5 is a flow chart of a method 300 of forming a bodily implant according to an embodiment. In one embodiment, the method includes, at step 310, forming a substrate. The substrate may be formed using any known method. For example, the substrate may be formed by cutting a mesh material in a shape to form the substrate.

At step 320, objects configured to reflect energy of a detection device is disposed within the carrier. In one embodiment, air bubbles are disposed or trapped within a carrier. In one embodiment, the carrier is a liquid polyurethane. In one embodiment, the air bubbles are disposed or trapped within the carrier by mixing the liquid polyurethane with a tool such as a drill tool or a dremel tool. In some embodiments, the liquid polyurethane is mixed with the tool on high speed. In some embodiments, a drill tool with a 3 mm drill bit is used to mix the carrier. In other embodiments, a spatula or other mixing tool may be used to mix the carrier to trap air bubbles within the carrier.

In some embodiments, the carrier is mixed until the carrier is saturated with air bubbles. In some embodiments, the carrier is mixed for a period of 1 to 2 minutes to trap air within the carrier. In other embodiments, the carrier is mixed for longer than 1 to 2 minutes. In yet other embodiments, the carrier is mixed for less than 1 to 2 minutes.

At step 330, the carrier having the air disposed or trapped therein is applied to the substrate. In some embodiments, drops of the liquid carrier are placed on the substrate. In some embodiments, the carrier is then dried by placing the substrate, with the carrier disposed thereon, in an oven at 100° C. In other embodiments, the substrate, with the carrier disposed thereon, is placed in an oven at a temperature greater than 100° C. In other embodiments, the substrate, with the carrier disposed thereon, is placed in an oven at a temperature less than 100° C. In some embodiments, the drying of the liquid carrier coupled the carrier to the substrate. In other embodiments, the carrier is not a liquid and another means, such as an adhesive, is used to couple the carrier to the substrate.

In some embodiments, the drops of the liquid carrier are placed on the substrate in a pattern. In some embodiments, the pattern or patterns of the liquid carrier on the substrate facilitate the identification of different portions of the substrate with the ultrasound device. For example, one end portion of the substrate may have the carrier disposed thereon in first pattern, another end portion of the substrate may have the carrier disposed thereon is a second pattern, and the medial portion of the substrate may have the carrier disposed thereon in a third pattern. Thus, the end portions and the medial portion of the substrate may be identified via the ultrasound device. In some embodiments, only portions, such as the medial or end portions, of the substrate include the carrier. In some embodiments, the liquid carrier is applied or disposed on the entire substrate. In some embodiments, the carrier is applied or disposed along the perimeter of the substrate.

In some embodiments, the applying the carrier to the substrate includes disposing the carrier in the spaces defined by the mesh substrate.

Figure 6:
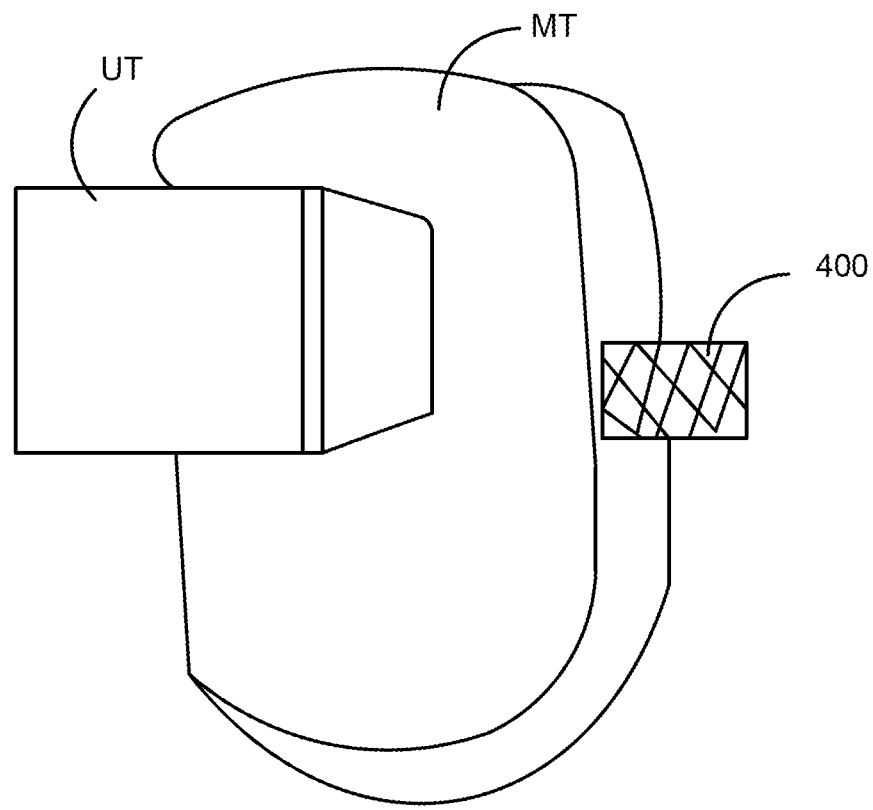
FIG. 6 illustrates an ultrasound device being used to view an implant disposed within muscle tissue.

As illustrated in FIG. 6, an ultrasound device UD may be used to view an implant 400 disposed within muscle tissue MT. Specifically, the ultrasound device UD is placed proximate muscle tissue MT that includes an implant 400 disposed therein. While FIG. 6 illustrates the ultrasound device UD being used muscle tissue MT that is not disposed within a body of a patient, it should be understood that an ultrasound device may be used to view an implant disposed within a body of a patient (i.e., muscle tissue that is disposed within the body of the patient).

In some embodiments, an implant includes a substrate and a carrier coupled to the substrate. The carrier includes a plurality of objects configured to reflect energy emitted by an ultrasound device.

In some embodiments, the substrate includes a mesh material. In some embodiments, the substrate includes a plastic material. In some embodiments, the substrate includes a polypropylene mesh material. In some embodiments, the substrate is configured to be placed within a body of a patient. In some embodiments, the substrate is configured to be placed within a pelvic region of a patient.

In some embodiments, the carrier includes polyurethane. In some embodiments, the substrate includes a mesh material. The mesh material defines openings and the carrier is disposed within the openings defined by the mesh material.

In some embodiments, the plurality of objects is a plurality of air bubbles. In some embodiments, the carrier includes a radio-opaque material.

In some embodiments, a method of forming a bodily implant includes (1) forming a substrate, (2) disposing a plurality of air bubbles within a carrier, and (3) applying the carrier to the substrate.

In some embodiments, the carrier is a liquid carrier, the method further includes allowing the liquid carrier to dry and couple to the substrate. In some embodiments, the applying the carrier to the substrate includes coupling the carrier to the substrate. In some embodiments, the forming a substrate includes cutting a mesh material to form the substrate. In some embodiments, the carrier is a liquid carrier and the disposing a plurality of air bubbles within a carrier includes mixing the liquid carrier. In some embodiments, the carrier is a liquid carrier and the disposing a plurality of air bubbles within a carrier includes mixing the liquid carrier with a drill motor. In some embodiments, the carrier is a liquid carrier and the disposing a plurality of air bubbles within a carrier includes mixing the liquid carrier with a spatula.

In some embodiments, the substrate includes a mesh material, the mesh material defining openings, the applying the carrier to the substrate includes disposing the carrier within at least one of the openings defined by the mesh material. In some embodiments, the disposing a plurality of air bubbles within a carrier includes disposing a plurality of air bubbles within a liquid polyurethane material. In some embodiments, the applying the carrier to the substrate includes depositing drops of the carrier onto the substrate. In some embodiments, the disposing a plurality of air bubbles within a carrier includes trapping air bubbles within a plastic material.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. An implant, comprising:
   a substrate including a mesh material defining a plurality of interstices; and
   a carrier coupled to the substrate, the carrier including a first carrier portion disposed on the substrate at a first location and a second carrier portion disposed on the substrate at a second location, the second location being disposed a distance from the first location, each of the first and second carrier portions including at least one object configured to reflect energy emitted by an ultrasound device,
   wherein the substrate includes a perimeter portion and a middle portion disposed a distance away from the perimeter portion, the perimeter portion extending around a perimeter of the substrate such that the perimeter portion surrounds the middle portion, the first carrier portion being coupled to the perimeter portion, the second carrier portion being coupled to the middle portion.

2. The implant of claim 1, wherein the mesh material includes a polypropylene mesh material.

3. The implant of claim 1, wherein the substrate is configured to be placed within a body of a patient.

4. The implant of claim 1, wherein the substrate is configured to be placed within a pelvic region of a patient.

5. The implant of claim 1, wherein the carrier includes polyurethane.

6. The implant of claim 1, wherein the at least one object includes a plurality of air bubbles.

7. The implant of claim 1, wherein the at least one object includes a radio-opaque material.

8. The implant of claim 1, wherein the substrate includes a first end portion, a second end portion, the middle portion being disposed between the first end portion and the second end portion, the middle portion having a width that is larger than a width of the first end portion and the second end portion.

9. The implant of claim 1, wherein the carrier includes a liquid-based material disposed on the substrate such that drying of the liquid-based material couples the carrier to the substrate.

10. The implant of claim 1, wherein the first carrier portion is coupled to the perimeter portion such that the first carrier portion extends around the perimeter of the substrate.

11. An implant, comprising:
a substrate including a mesh material defining a plurality of interstices and a plurality of intersections of the mesh material; and
a first carrier portion coupled to the mesh material at a first location, the first carrier portion defining air bubbles configured to reflect energy emitted by an ultrasound device;
a second carrier portion coupled to the mesh material at a second location, the second carrier portion defining air bubbles configured to reflect energy emitted by the ultrasound device, the second location being disposed a distance from the first location,
wherein the substrate includes a perimeter portion and a middle portion disposed a distance away from the perimeter portion, the perimeter portion extending around a perimeter of the substrate such that the perimeter portion surrounds the middle portion, the first carrier portion being coupled to the perimeter portion, the second carrier portion being coupled to the middle portion.

12. The implant of claim 11, wherein the first location is a first intersection of the plurality of intersections and the second location is a second intersection of the plurality of intersections such that the first intersection is disposed a distance from the second intersection.

13. The implant of claim 11, wherein the first location is a first interstice of the plurality of interstices and the second location is a second interstice of the plurality of interstices such that the first interstice is disposed a distance from the second interstice.

14. The implant of claim 11, wherein the first carrier portion includes a liquid-based material having the air bubbles such that drying of the liquid-based material couples the first carrier portion to the substrate.

15. The implant of claim 11, wherein the first carrier portion is coupled to the perimeter portion such that the first carrier portion extends around the perimeter of the substrate.

16. An implant, comprising:
a substrate including a first end portion, a second end portion, and a middle portion disposed between the first end portion and the second end portion, the middle portion having a width that is larger than a width of the first end portion and the second end portion; and
a plurality of carrier portions including a first carrier portion, a second carrier portion, and a third carrier portion, the first carrier portion having objects configured to reflect energy emitted by an ultrasound device that are arranged in a first pattern, the second carrier portion having objects configured to reflect energy emitted by the ultrasound device that are arranged in a second pattern, the third carrier portion having objects configured to reflect energy emitted by the ultrasound device that are arranged in a third pattern, wherein the first pattern, the second pattern, and the third pattern are different patterns,
the first carrier portion being disposed on the first end portion of the substrate, the second carrier portion being disposed on the second end portion of the substrate, the third carrier portion being disposed on the middle portion of the substrate.

17. The implant of claim 16, wherein the objects of the first carrier portion are air bubbles.

18. The implant of claim 16, wherein each of the plurality of carrier portions includes a liquid-based material disposed on a respective portion of the substrate such that drying of the liquid-based material couples each carrier portion to the respective portion of the substrate.

* * * * *